(12) United States Patent
Anson

(10) Patent No.: US 6,334,867 B1
(45) Date of Patent: *Jan. 1, 2002

(54) SURGICAL GRAFT/STENT SYSTEM

(75) Inventor: Anthony Walter Anson, Hounslow (GB)

(73) Assignee: Anson Medical Ltd (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/036,588

(22) Filed: Mar. 6, 1998

(51) Int. Cl.[7] .................................................. A61F 2/06
(52) U.S. Cl. ...................................... 623/1.13; 623/1.15
(58) Field of Search ......................... 623/1, 1.13, 1.15, 623/1.18, 1.1, 1.11, 1.12; 606/198

(56) References Cited

U.S. PATENT DOCUMENTS

| | | | |
|---|---|---|---|
| 5,167,614 A | | 12/1992 | Tessmann et al. .............. 604/8 |
| 5,653,743 A | * | 8/1997 | Martin ............................ 623/1 |
| 5,700,285 A | * | 12/1997 | Myers et al. .................... 623/1 |
| 5,709,713 A | * | 1/1998 | Evans et al. .................... 621/1 |
| 5,755,770 A | * | 5/1998 | Ravenscroft .................... 623/1 |
| 5,782,904 A | * | 7/1998 | White et al. ................. 623/1 X |
| 5,824,040 A | | 10/1998 | Cox et al. ....................... 623/1 |
| 5,833,707 A | * | 11/1998 | McIntyre et al. ............ 606/198 |
| 5,948,018 A | * | 9/1999 | Dereume et al. ............... 623/1 |
| 6,187,033 B1 | * | 2/2001 | Schmitt et al. ................. 623/1 |

FOREIGN PATENT DOCUMENTS

| | | |
|---|---|---|
| EP | 0 326 426 A2 | 8/1989 |
| EP | 0 461 791 A1 | 12/1991 |
| EP | 0 621 017 A1 | 10/1994 |

* cited by examiner

*Primary Examiner*—Corrine McDermott
*Assistant Examiner*—Hieu Phan
(74) *Attorney, Agent, or Firm*—Craig A. Fieschko, Esq.; DeWitt Ross & Stevens S.C.

(57) ABSTRACT

A tubular graft/stent includes a tubular sheath (10) having at intervals along its length a plurality of ring-like rigid members (11), which are attached to the sheath around their respective circumferences and are made of a shape memory material, so that when the members (11) change shape the sheath (10) adopts a new cross section in conformity with them along its whole length. The members may be discontinuous to allow the adoption of a contracted shape in the martensitic phase and an expanded shape in the austenitic phase. A graft may also have a side tube (14) which can be inverted so as to be housed within the sheath.

16 Claims, 3 Drawing Sheets

SURGICAL GRAFT/STENT SYSTEM

BACKGROUND

Field of the Invention

This invention relates to a graft/stent system for use in human or animal surgery. One example of this type of graft/stent is disclosed in EP 0326426A which describes an artificial blood vessel in the form of a tubular sheath having a ring-like member located at each of its two ends. Another example, disclosed in EP 0461791A, is an aortic graft with one of its tubular ends divided into two branches.

SUMMARY

According to an aspect of the present invention, there is provided a tubular graft/stent as specified in claim 1.

According to another aspect of the present invention, there is provided a tubular graft/stent as specified in claim 9.

The invention proposes a medical tubular graft stent which comprises a tubular sheath having at intervals along its length a plurality of ring-like rigid members, wherein said members are attached to the sheath around their respective circumferences and are made of a shape memory material, so that when said members change shape, the sheath adopts a new cross-section in conformity with them along its whole length.

Preferably, this provides a compliant tubular sheath, into which a series of open rings are integrated. The rings act as rigidising members and are capable of being radially compressed by mechanical forces in the martensitic phase so as to reduce the diameter, and of then returning in the austenitic phase to a memorised, larger diameter by a thermal effect.

In a further aspect, the invention proposes a tubular graft comprising a tubular sheath having a branch tube which is sufficiently flexible to be inverted so as to be housed within the sheath during an insertion operation in a human or animal body, and to be redeployed as a branch after said operation. The sheath and/or the branch tube may employ annular rigid members of a shape memory material, as explained above. In all cases, the members are preferably discontinuous, e.g. a ring with a break so as to facilitate compression and re-expansion.

In order that the invention shall be clearly understood, several exemplary embodiments thereof will now be described with reference to the accompanying drawings, in which:

DETAILED DESCRIPTION OF THE PREFERRED EMBODIMENTS

Figure 1:
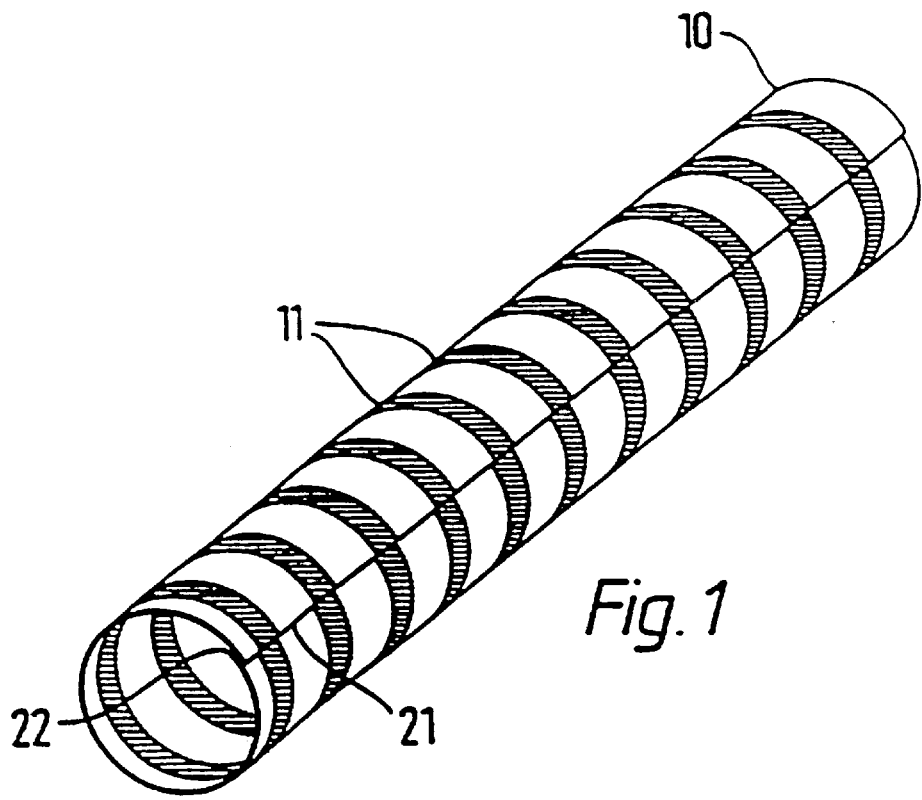
FIG. 1 shows a perspective view of a first form of graft.

An exemplary general arrangement is shown in FIG. 1. A compliant tube 10 can be constructed of any flexible material such as cloth, polymers, elastomers or gels. Secured within the compliant tube are a plurality of expandable or contractible open rings 11 composed of shape memory alloy material. The shape memory alloy rings give structural support to the compliant tubular sheath and are oriented transverse to the axis of the tube. The cube is circumferentially closed by the overlap 20, but has free edges 21, 22. Alternatively, the edges 21, 22 might butt one another, but this does not provide as much certainty that the tube wall is closed.

The compliant tube 10 can be generated by fabrication methods, or an "open" tube could be made by using flat sheets whose shape is established by the shape memory alloy rings. The tubular form might also use sheets of dissimilar materials. The cube may be produced in continuous lengths and cut off as needed.

The shape memory alloy rings can be retained by casting a suitable compliant material around the rings, by adhesive bonding, sewing or by generating a series of pockets within which the rings may be held by welding, sewing, mechanical fixation or adhesive bonding. In the embodiment shown, the rings 11 are in a single piece, but could be in two or more arcuate sections.

Figure 2:
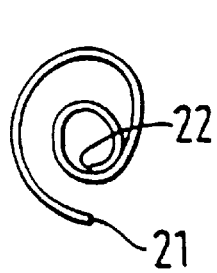
FIG. 2 shows its compressed form in the martensitic phase in transverse cross-section.
Figure 3:
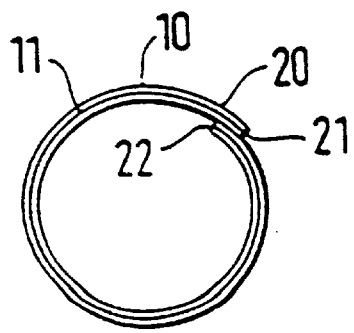
FIG. 3 shows its expanded form in the austenitic phase.

FIGS. 2 and 3 show the compressed (e.g. spiral or rolled-up) and expanded forms of the tube. The tubular graft/stent is radially compressed down to 5.5 mm outside diameter before the device is fitted into the human body via a delivery catheter. In its expanded form, the outside diameter might be up to 4 cm.

The device described is suitable for a number of minimally invasive surgical techniques or may substantially reduce trauma associated with the introduction of implanted medical devices within a living organism. A single, plain tube (known as a tubular graft) with integrated expandable contractible rings (known as stents) as described is inserted into an occluded fluid carrying vessel or a vessel that has a structure. When appropriately positioned via the catheter, heat from the human body (or a heated fluid introduced) will cause the latent geometry of the shape memory alloy to be re-called. Under these circumstances the rings will expand to a pre-determined position as seen in FIG. 3, the outside dimensions of which will be slightly larger than the inner dimensions of the fluid carrying vessel. Frictional effects will normally retain the graft/stent in position. However, the shape memory alloy may be arranged so that when a thermal transition point (memory re-call) is reached selected sections of the alloy will protrude from the metals surface presenting a substantial fixation force. One or more of the alloy rings could be configured with this additional retention feature.

This device may find applications in surgical repair or maintenance procedure for the human body or other animal species. Gastro-intestinal system connections, oesophageal cancer, aneurysms, coronary by-pass connections and other vascular by-pass or shunt procedures could employ the stent/graft device.

The dynamic properties of the rings expand the graft/stent within the body to effect an opening of constricted or occluded vessel. The outer graft sheath would assist in preventing occlusive material from once again entering the vessel. The compliant sheath will also exclude tumorous growth, maintaining luminal patency.

Figure 4:
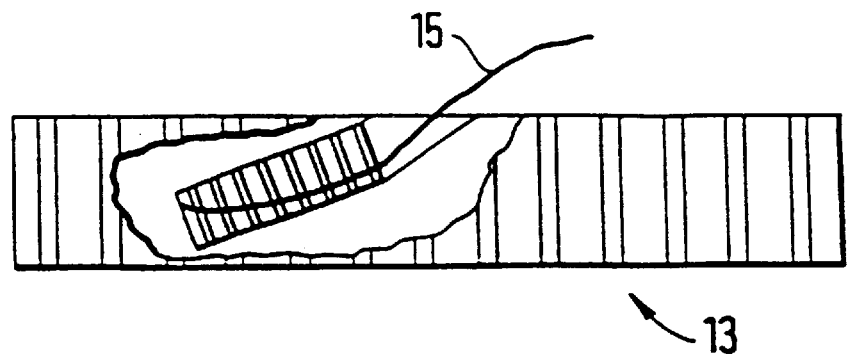
FIG. 4 shows an embodiment having a branch tube in its inverted position.
Figure 5:
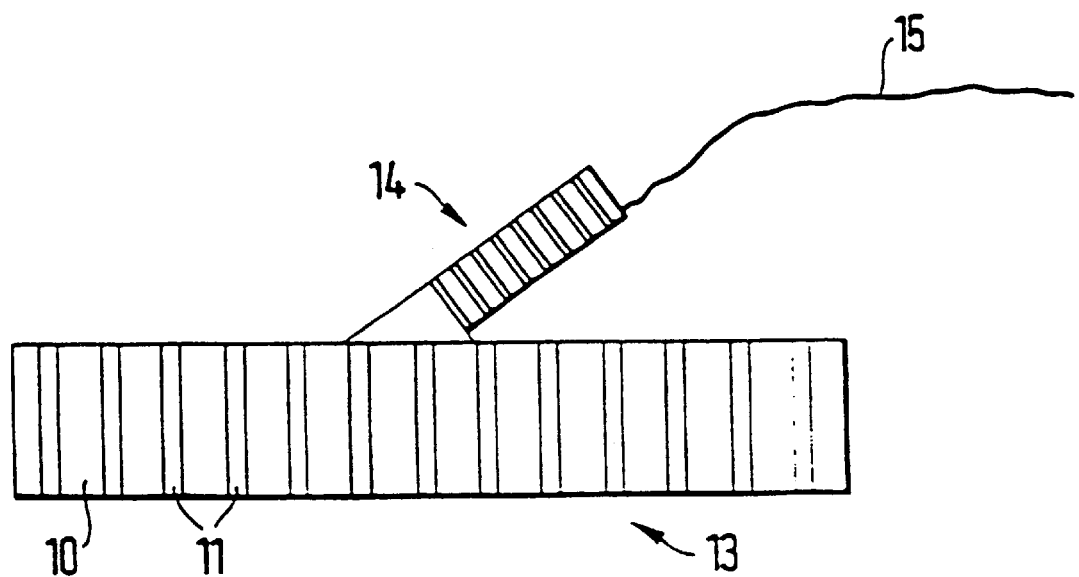
FIG. 5 shows the FIG. 4 version with the branch tube deployed.

The tubular graft with in integrated shape memory alloy rings may be a simple tube-like form as described or could be a manifold system having a main tube 13 from which one or substantial numbers of connections 14 may be made, as seen in FIGS. 4 and 5. The single a tube or manifold will allow fluids to pass in or out of the said connections, to or from the main tube structure. The branches extending from the main body can be of uniform cross-section or of tapering construction.

A tubular graft of the type described might be simply bifurcated or may have numerous smaller or larger tubes of similar construction, attached to the main tube body. The branches attached to the body of the device may have a similar shape memory alloy ring configuration. Each branch 14 can be inverted so as to fit within the main tube. Under these conditions, the whole assembly can be radially compressed, the manifold system now appearing as a single tube for initial insertion via a catheter. A suitable cord to 15 is connected to the inverted branch enabling it/them to be re-inverted by pulling the cord, as shown in FIG. 5. Preferably, the rings nearer to the main tube are largest and are progressively smaller towards the end, to allow the inversion to occur.

When warmed, the shape memory alloy rings will expand to a pre-determined position. If employed in a surgical repair, forces exerted by the shape memory alloy rings will be of sufficient magnitude to open an occluded vessel thus enabling appropriate fluid flows to continue.

The compliant outer sheath would enable radial or axial movement of the vessel to occur. This might be the case if the stent/graft were positioned in an osophagus that had radially disposed tumours. Peristalsis effects used to assist transportation of food and liquids in the human body would need to be maintained in oesophageal dysfunctional problems. The covered or sheathed stent system would exclude tumorous in-growth and still enable peristalsis to occur.

The compliant could be 0.050 mm polyurethane, polyester or polythene. The shape memory material may be a metal alloy with this property, or alternatively certain mouldable plastics materials such as homopolymers of lactide or glycolide, or copolymers of lactide and glycolide.

The invention is also considered to include a graft with a side tube which does not employ stents of shape memory material. Thus in addition to shape memory materials, the ring-like rigid members 11 can also be fabricated from elastic materials such as stainless steel or the super-elastic forms of nickel-titanium alloys. In this case the implant is constrained within in outer sheath after whose removal the graft will expand to adopt its final shape.

Figure 6:
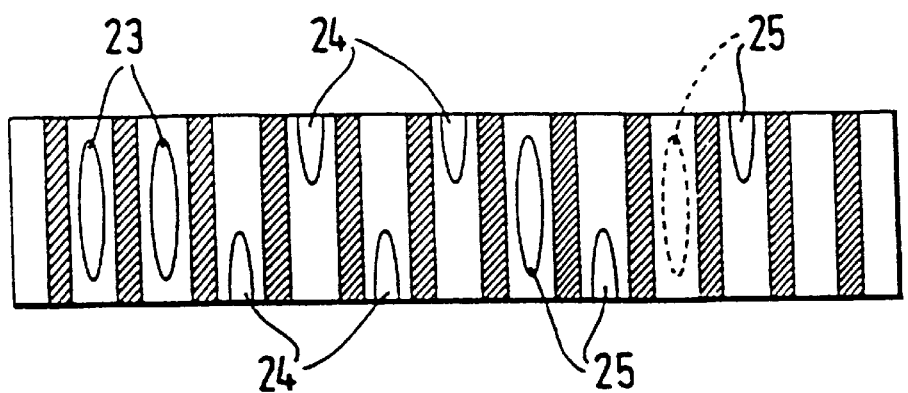
FIG. 6 shows a further embodiment of the present invention.

In the embodiment of FIG. 6, which is of particular benefit in stenting tortuous vessels such as the male urethra, the flexible tubular sheath can contain slits or openings 23 which are approximately parallel to the ring-like members and which allow greater flexion of the implant without kinking the sheath. The arrangement of the slits or openings can be varied with the application and can be positioned to be all on one side of the cube 23, on alternating sites 24 or spirally arranged along the sheath (25). Other arrangements are possible.

The overlap 20 can be designed to have one of three properties:

1) The overlap can be left to slide freely over itself, permitting the graft assembly to be contracted by muscles in the vessel or to allow pressure pulses in arterial blood, arising from the heartbeat, to be transmitted to the artery wall. The action of pressure pulses is involved in maintaining the vasomotor tone in blood vessels.

The mating surfaces of the overlapping part of the sheath can be coated to reduce friction and wear with materials such as PTFE or diamond-like coatings.

Figure 7:
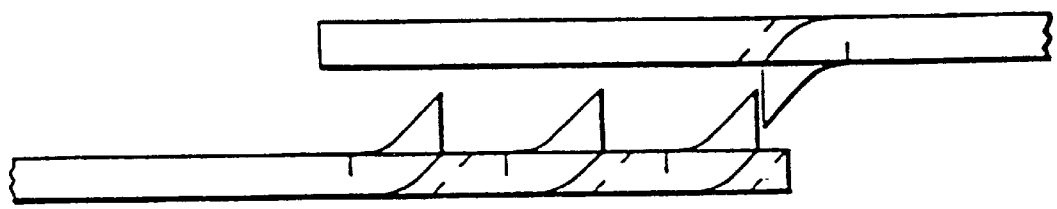
FIGS. 7 and 8 show enlarged and developed views of two versions of an overlap region.

2) As shown in FIG. 7, the overlap can incorporate a ratchet-like mechanism which will allow the diameter of the ring-like rigid member to expand but not to contract. This will guarantee that the lumen of the vessel will be maintained to a minimum diameter and will allow the ring to be locked against the inside of the vessel wall to prevent migration of the device.

Figure 8:
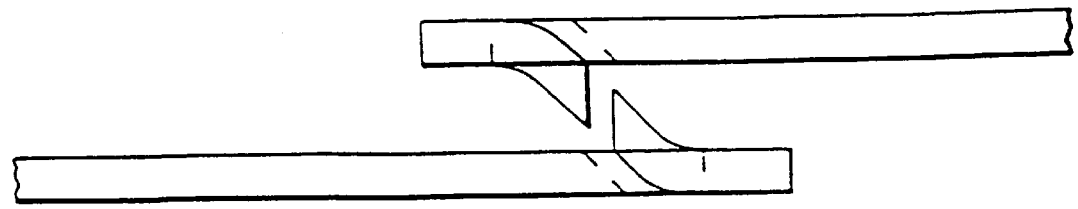

3) As shown in FIG. 8, the overlap can incorporate a ratchet-like mechanism which will allow the diameter of the ring-like rigid member not to exceed a specified diameter. This is of use where the vessel is fragile and can be exposed to high intraluminal pressures.

The ratchet-like mechanism can be incorporated onto the walls of the sheath by moulding, machining, or attaching ratchet components. Alternatively, the ratchet mechanism can be formed in the ends of the ring-like member and can be either permanently present or deployed by the action of thermal memory.

An implant can be assembled which incorporates a combination of all three types of overlap mechanism so that for instance, the distal ends of the graft can use ratchet expanding rings to lock the device in place, while the main body of the graft uses alternating sliding and diameter-limiting rings to allow limited transmission of pulsatility while restricting the maximum diameter of the graft.

The benefit of the graft can be increased by incorporating coatings onto its inner or outer surfaces. These coatings can be biomimetics such as phosphorylcholines and proteins, organic biocompatibles such as hydrophilic plastics and inorganic coatings, such as diamond-like carbon. The coatings can be used to be thrombus-resistant, encrustation resistant or to promote cellular ingrowth. In addition, the coatings can be used to release locally acting pharmacological agents and they can be multiply layered.

Deployment of the inverted segment 14 can be achieved by adding a short handle, tab or strip to the distal end of the side branch which can be engaged by a snare, forceps or similar engagement means.

What is claimed is:

1. A tubular graft/stent comprising:
   a tubular sheath that is a graft/stent; and
   an integral branch tube having an end fixed to the tubular sheath at an opening in a side wall of the tubular sheath, wherein the branch tube is a graft/stent along its entire length, the branch tube comprising a plurality of rigid ring-like members being of progressively smaller size in the direction progressively away from the tubular sheath, and the branch tube being sufficiently flexible to be fully inverted along its entire length so as to be fully housed within the tubular sheath during an insertion operation in a human or animal body, and to be redeployed as a branch after said insertion operation.

2. A tubular graft/stent according to claim 1, wherein the rigid ring-like members are made of a shape memory material, so that when said members change shape the sheath adopts a new cross-section in conformity with them along its whole length.

3. A tubular graft/stent according to claim 1, wherein the rigid members are attached to the sheath around their respective peripheries.

4. A tubular graft/stent according to claim 1, wherein said members are discontinuous to allow them to adopt a contracted shape in the martensitic phase, and an expanded shape of larger circumference in the austenitic phase.

5. A tubular graft/stent according to claim 1, wherein said members can be caused to adopt a spiral form as the contracted shape and a generally circular form as the expanded shape.

6. A tubular graft/stent according to claim 1, wherein the rigid ring-like members are embedded in a compliant material that is cast around said members to form the sheath.

7. A tubular graft/stent according to claim 1, wherein the rigid ring-like members are held in pockets formed in the material of the sheath.

8. A tubular graft/stent according to claim 1, wherein the members are trapped between two layers of material which together form the sheath.

9. A tubular graft/stent according to claim 1, wherein the members include portions which project from the outer surface of the graft in its new cross-section, such projecting portions forming anchors for locating the graft in position in a body.

10. A tubular graft/stent according to claim 1, wherein the branch tube has a draw string attached at its free end such that when inverted into the sheath the draw string may be pulled to redeploy the branch tube outside the sheath.

11. A method of inserting a graft/stent having a tubular sheath which is a graft/stent and an attached integral branch tube that is also a graft/stent along its entire length, the method comprising:

fully inverting said branch tube along its entire length to place said branch tube fully within said tubular sheath for insertion in a body;

inserting said graft/stent into said body; and pulling said branch tube out of said tubular sheath in said body, wherein pulling said tubular branch tube re-inverts said branch tube and leaves said branch tube attached to said tubular sheath.

12. The method of claim 11, wherein pulling said branch tube comprises:

engaging a cord on a distal end of said branch tube; and pulling said cord to deploy said branch tube within said body.

13. The method of claim 12, wherein said cord is selected from the group consisting of a draw string, short handle, tab, and strip.

14. The method of claim 11 wherein the sheath includes at least one ring-like member along its length which is made of a shape memory material, and wherein the method further comprises the step of cooling the member.

15. The method of claim 11 wherein the sheath includes at least one ring-like member along its length, the member having a variable shape wherein it may be at least partially coiled, wherein the method further comprises the step of uncoiling the member.

16. The method of claim 11 wherein the sheath is defined by material which is at least partially coiled, wherein the method further comprises the step of uncoiling the sheath from a small-diameter state to a large-diameter state.

* * * * *